United States Patent [19]

Scotese et al.

[11] Patent Number: 4,621,142

[45] Date of Patent: Nov. 4, 1986

[54] PRECURSORS OF BENZO- AND THIENO-FUSED HETEROCYCLIC ANTI-ULCER AGENTS

[75] Inventors: Anthony C. Scotese, King of Prussia; Arthur A. Santilli, Havertown; Donald P. Strike, St. Davids, all of Pa.

[73] Assignee: American Home Products Corporation, New York, N.Y.

[21] Appl. No.: 760,709

[22] Filed: Jul. 30, 1985

Related U.S. Application Data

[63] Continuation-in-part of Ser. No. 564,120, Dec. 21, 1983, abandoned.

[51] Int. Cl.$^4$ .......................................... C07D 495/04
[52] U.S. Cl. ..................................... 546/198; 544/58.4; 544/133; 544/135; 548/181; 548/212
[58] Field of Search ............... 546/198; 544/58.4, 133, 544/135; 548/181, 212

[56] References Cited

U.S. PATENT DOCUMENTS 4,490,527 12/1984 Schiehser et al. .............. 546/198 X

*Primary Examiner*—Richard A. Schwartz
*Attorney, Agent, or Firm*—George Tarnowski

[57] ABSTRACT

A process for preparing certain benzo- and thieno-fused heterocyclic compounds having $H_2$-receptor antagonist and antisecretory activity, which comprises the amide reduction of N-substituted carbamoyl-containing benzo- or thieno-fused heterocyclic intermediates; and said N-substituted carbamoyl-containing benzo- or thieno-fused heterocyclic intermediates.

5 Claims, No Drawings

PRECURSORS OF BENZO- AND THIENO-FUSED HETEROCYCLIC ANTI-ULCER AGENTS

This is a continuation-in-part of U.S. Ser. No. 564,120, filed Dec. 21, 1983, now abandoned.

This invention relates to a novel process for the preparation of certain benzo-and thieno-fused heterocyclic compounds and to intermediates useful in the process. The products are disclosed in U.S. Pat. No. 4,490,527. The process of the present invention gives the products in good overall yield from conveniently available starting materials.

The present invention provides a process for the preparation of benzo-and thieno-fused heterocyclic compounds of the formula

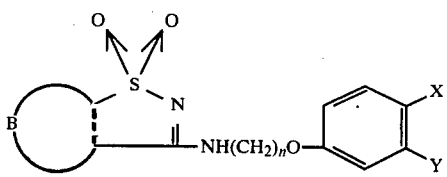

wherein
B is a moiety having the formula

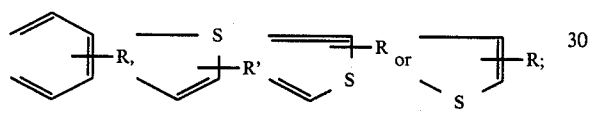

R is mono- or dihalo, nitro, cyano, trifluoromethyl, lower alkyl, lower alkoxy, lowercycloalkyl, mono- or di-lower alkyl substituted amino, lower alkyl thio, loweralkylsulfonyl, sulfamoyl, lower alkyl substituted sulfamoyl, phenyl or phenyl substituted with halo, lower alkyl, lower alkoxy, trifluoromethyl, cyano or nitro;

X and Y are each, independently, hydrogen or

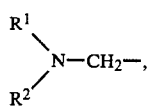

wherein $R^1$ is hydrogen or lower alkyl; $R^2$ is hydrogen or loweralkyl; or $R^1$ and $R^2$ taken together form a heterocyclic moiety selected from the group 1-pyrrolidinyl, 1-piperidinyl, 1-hexahydroazepinyl, 1-octahydroazocinyl, 3-thiazolidinyl, 4-morpholinyl or 5-thiomorpholinyl, with the proviso that one of X and Y is always hydrogen;

n is 1 to 4;

and the pharmacologically acceptable salts thereof, and intermediates which are used in said process.

The process comprises (A) reacting a compound of the formula

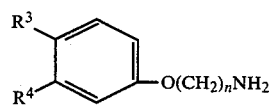

wherein n is as defined hereinbefore; and
$R^3$ and $R^4$ are, independently, hydrogen or

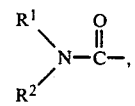

wherein $R^1$ and $R^2$ are as defined hereinbefore, with the proviso that one of $R^3$ and $R^4$ is always hydrogen, with (i) a compound having the formula

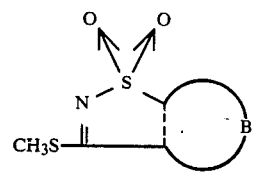

wherein B is as defined hereinbefore, to yield a compound having the formula

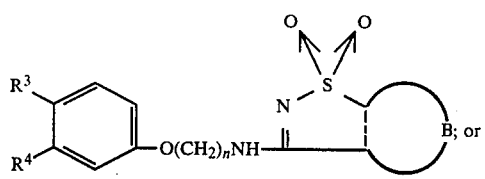

(ii) a compound having the formula

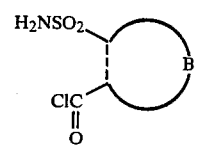

wherein B is as defined hereinbefore to yield a compound having the formula

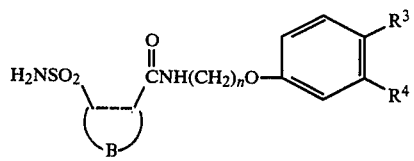

which compound is subjected to ring closure to yield a compound having the formula

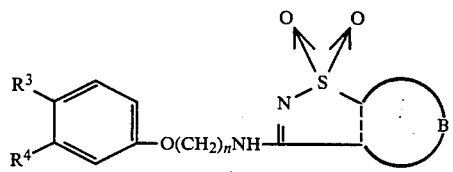

(B) subjecting the compound obtained in A(i) or (ii) to amide reduction to obtain a compound having the formula

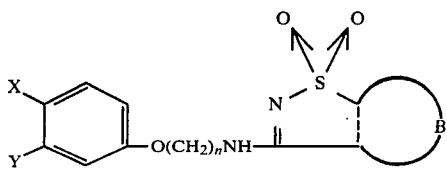

wherein X, Y, B and n are as defined hereinbefore and, if desired, converting the free base compounds into pharmacologically acceptable salts thereof.

The term "halo" refers to fluoro, chloro and bromo. The terms "lower-alkyl" and "loweralkoxy" refer to moieties having 1 to 6 carbon atoms in the carbon chain. The term "lower cycloalkyl" refers to cyclic structures having 5 to 7 carbon atoms. The term "alkanoyl" refers to the moiety RCO— wherein R is an alkyl group having 1 to 4 carbon atoms.

In the reaction sequence in which the 1-aminoalkyoxy-3-N-substituted carbamoyl benzene intermediate is reacted with the methylthio derivative of a thienoisothiazole 1,1-dioxide to yield an intermediate having the partial structure

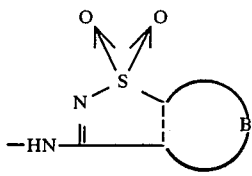

the reaction is carried out in an organic solvent under reflux conditions. The resulting product is purified by conventional recrystallization techniques. In the reaction sequence in which the reacting intermediate is an aminosulfonyl-thiophene carbonyl chloride and which yields an intermediate having the partial structure

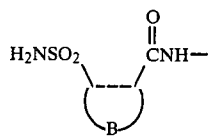

the reaction is carried out in an inert organic solvent, for example, tetrahydrofuran, at room temperature. The compound obtained is purified by conventional techniques, and is then subjected to ring closure to form the isothiazole S',S'-dioxide ring:

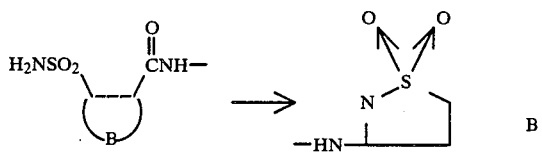

This preferably carried out using phosphorus oxychloride as the ring closing agent and the reaction is run under reflux. The product obtained is identical to the intermediate that is prepared using the methylthio derivative of a thienoisothiazole 1,1-dioxide.

The intermediate amide discussed immediately supra, whether obtained by the one or the other of the reaction sequences, is then subjected to amide reduction to reduce the carbonyl formation of the N-substituted carbamoyl moiety to the methylene function:

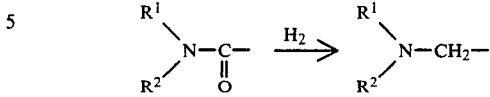

This is carried out by reacting the amide intermediate with phosphorus oxychloride to form a reactive mono- or dichloro intermediate which is then subjected to reduction with a mild reducing agent, for example, sodium borohydride. The final product is recovered and purified by techniques conventional in the art.

The final products obtained in their free base form can be converted into pharmacologically acceptable salts by standard procedures. For example, the free base can be dissolved in a suitable organic solvent and the solution treated with a solution of the selected acid, in accordance with conventional procedures for preparing pharmacologically acceptable salts. As examples of suitable acids, there may be used hydrochloric, hydrobromic, sulfuric, nitric, phosphoric, acetic, maleic, fumaric, citric, methanesulfonic, p-toluenesulfonic and the like.

The starting compound thienoisothiazole 1,1-dioxide derivatives can be prepared from commercially available compounds. Thus, for example, the methylthio derivatives of the thienoisothiazole 1,1-dioxides can be prepared in the following manner from available starting material:

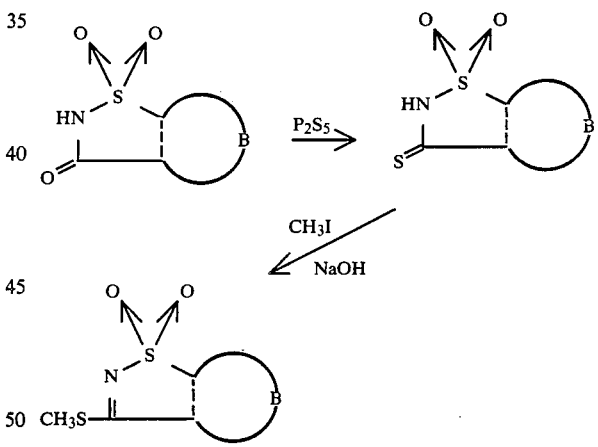

where B is as defined hereinbefore.

The starting compound 1-aminoalkoxy-3-N-substituted carbamoyl benzenes similarly, can be prepared from available materials by conventional techniques. The following reaction sequence is illustrative:

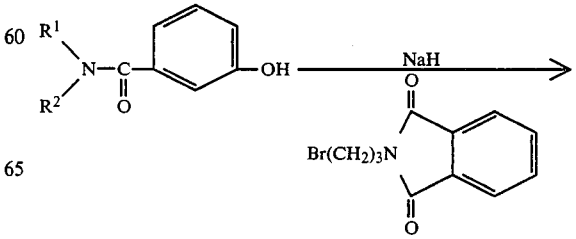

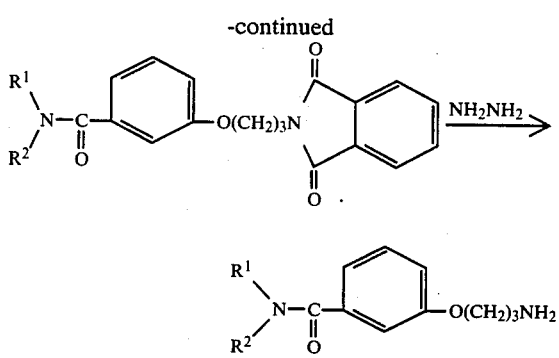

The reaction is carried our in an inert organic solvent, e.g., dimethylformamide and the desired intermediate product is recovered and purified by conventional techniques.

The process of the invention can be used to prepare compounds such as those disclosed in U.S. Ser. No. 468,221 and which have been described, supra. These compounds are potent $H_2$-receptor antagonists and antisecretory agents, which are useful in the treatment of conditions where there is hypersecretion of gastric acid, such as in gastric and peptic ulceration, and other conditions caused or exacerbated by gstric acidity, such as stress ulceration or gastric intestinal bleeding due to trauma.

The following examples illustrate this invention.

PREPARATION OF THIOPHENE AND THIENOISOTHIAZOLE 1,1-DIOXIDE INTERMEDIATES

I. 4-(Aminosulfonyl)-3-thiophenecarbonyl chloride (A) 4-(aminosulfonyl)-3-thiophenecarboxylic acid Preparation is according to the method disclosed in U.S. Pat. No. 4,028,373. A solution of 0.5 g. of 4-(aminosulfonyl)-3-thiophenecarboxylic acid methyl ester in 20 ml. of 10% aqueous sodium hydroxide is allowed to sit at room temperature for 3 days. The solution is acidified with concentrated hydrochloric acid. The precipitate which forms is collected to give 0.35 g. of product. A small amount is recrystallized twice from ethyl acetate (petroleum ether is added to the cloudy point to initiate precipitation) to give the analytical sample, m.p. 222°–224° C.

Analysis for: $C_5H_5NO_4S_2$. Calculated: C, 28.98; H, 2.43; N, 6.76. Found: C, 29.40; H, 2.54; N, 6.68.

(B) 4-(aminosulfonyl)-3-thiophenecarbonyl chloride

A mixture of 1 g. of 4-(aminosulfonyl)-3-thiophenecarboxylic acid in 20 ml of thionyl chloride is heated under reflux for 4 hours. The mixture is cooled to room temperature and is filtered. The filtrate is evaporated in a rotary evaporator and the residue is dissolved in 270 ml. of anhydrous ether. The solution is diluted with 200 ml. of petroleum ether and the precipitate which forms is collected to give 0.4 g. of product, m.p. 140; 262°–265° C.; mass spectrum CI m/e 226 MH+.

Analysis for: $C_5H_4ClNO_3S_2$. Calculated: C, 26.61; H, 1.79; N, 6.21. Found: C, 27.24; H, 1.91; N, 6.26.

II. 3-(Methylthio)thieno[3,4-d]isothiazole 1,1-dioxide (A) Thieno[3,4-d]isothiazol]3(2H)-thione 1,1-Dioxide To a mixture of 5.6 g. (0.03 mole) of thieno[3,4-d]iso-thiazol-3(2$\underline{H}$)-one 1,1-dioxide in 50 ml. of dry pyridine is added 5.6 g. (0.016 mole) of phosphorus pentasulfide portionwise over 3 minutes. The viscous mixture is slowly heated in an oil bath under an atmosphere of nitrogen. The temperature of the oil bath is slowly increased to 80° C. after 30 minutes. The temperature of the oil bath is then kept at 80° C. for 25 minutes, the internal temperature reading 63° C. The solution is cooled to 50° C. and is added dropwise over 5 minutes to 200 ml. of water and cooled in an ice bath. The precipitate which forms is collected and discarded. The filtrate is cooled in ice and acidified with concentrated hydrochloric acid to pH 1. The precipitate which forms is collected to yield 40% of material. In another experiment, a sample is recrystallized from water to obtain an analytical sample, m.p. 196°–8° C. (dec.).

Analysis for: $C_5H_3NO_2S_3$. Calculated: C, 29.26; H, 1.47; N, 6.82. Found: C, 29.91; H, 1.43; N, 6.87.

(2) 3-(Methylthio)thieno[3,4-d]isothiazole 1,1-dioxide

To a mixture of 0.9 g. (0.0044 mole) of thieno[3,4-d]isothiazole-3(2$\underline{H}$)-thione 1,1-dioxide in 4 ml. of ethanol is added a solution of 0.35 g. (0.0044 mole) of 50% sodium hydroxide in 3 ml. of water. To this thick mixture is added 0.62 g. (0.0044 mole) of iodomethane. The mixture is heated under reflux for 5 minutes, and then filtered to give 0.35 g. of product. On cooling, a second crop of 0.1 g. of material is obtained. A small amount of the first crop is recrystallized from ethanol to afford an analytical sample, m.p. 184°–6° C.

Analysis for: $C_6H_5NO_2S_3$. Calculated: C, 32.86; H, 2.30; N, 6.39. Found: C, 32.76; H, 2.27; N, 6.43.

PREPARATION OF 1-AMINOALKOXY-3-N-SUBSTITUTED CARBAMOYL BENZENE INTERMEDIATES

1-[[3-(3-aminopropoxy)phenyl]carbonyl]piperidine (A)

1-[3-[3-(1,3-dihydro-1,3-dioxo-2H-isoindol-2-yl)propoxy]benzoyl]piperidine

To a suspension of 0.09 g. (0.0024 mole) of 60% sodium hydride in 10 ml. of dry N,N-dimethylformamide is added dropwise over 5 minutes a solution of 0.5 g. (0.0024 mole) of 1-(3-hydroxybenzoyl)piperidine, prepared according to the method of G. Tilly, Chem. Ther. 2 (1), 57–65 (1967); C. A. 67 32432S, in 10 ml. of dry N,N-dimethylformamide. The mixture is stirred at room temperature for 5 minutes and then 0.64 g. (0.0024 mole) of N-(3-bromopropyl)phthalimide is added. The mixture is stirred at room temperature for 1 hour and is diluted with water to the cloudy point. The precipitate which forms is collected and is air dried to give 0.5 g. of product. A small amount is recrystallized from ethanol to give the analytical sample, m.p. 120°–122° C.

Analysis for: $C_{23}H_{24}N_2O_4$. Calculated: C, 70.39; H, 6.16; N, 7.14. Found: C, 70.07; H, 6.10; H, 7.24.

(B) 1-[[3-[3-aminopropoxy)phenyl]carbonyl]piperidine

To a warm solution of 0.5 g. of 1-[3-[3-(1,3-dihydro-1,3-dioxo-2H-isoindol-2-yl)propoxy]benzoyl]piperidine in 20 ml. of absolute ethanol is added 1 ml. of hydrazine. The mixture is stirred at room temperature for 1 hour and is filtered. The filtrate is allowed to stand at room temperature for 18 hours and again is filtered. The filtrate is evaporated in a rotary evaporator and the residue is partitioned between 50 ml. of ether and 50 ml. of water. The ether layer is dried over magnesium sulfate, is filtered and is evaporated to give 80 mg. of oil. The oil is purified by HPLC using 1-Silica Prep Pac (Waters) and a combination of methanol, ethyl acetate and 1% triethylamine to give the analytical sample.

Analysis for: $C_{15}H_{22}N_2O_2$. Calculated: C, 68.67; H, 8.45; N, 10.68. Found: C, 68.16; H, 8.50; N, 10.74.

EXAMPLE 1

1-[3-[3-(Thieno[3,4-d]isothiazol-3-ylamino)propoxy]-benzoyl]piperidine S',S'-dioxide Method A (1)

4-(Aminosulfonyl)-N-[3-[3-(1-piperidinylcarbonyl)-phenoxy]propyl]-3-thiophene-carboxamide, hydrate To a solution of 0.26 g. (0.001 mole) of 1-[[3-(3-aminopropoxy)phenyl]carbonyl]piperidine in 30 ml. of dry tetrahydrofuran is added 0.23 g. (0.001 mole) of 4-(aminosulfonyl)-3-thiophenecarbonyl chloride. The mixture is allowed to stand at room temperature for 15 minutes. The tetrahydrofuran is removed in a rotary evaporator and the residue is dissolved in 50 ml. of chloroform. The chloroform solution is extracted with 50 ml. of 10% aqueous sodium hydroxide solution followed by 50 ml. of 10% aqueous hydrochloric acid. The chloroform layer is washed with water, is dried over magnesium sulfate and is filtered. The filtrate is evaporated in a rotary evaporator to give 0.15 g. of an amorphous product, m.p. 70°-80° C.; mass spectrum CI m/e 452 MH+.

Analysis for: $C_{20}H_{25}N_3O_5S_2.H_2O$. Calculated: C, 51.16; H, 5.79; N, 8.95. Found: C, 51.58; H, 5.64; N, 8.45.

(2)

1-[3-[3-(Thieno[3,4-d]isothiazol-3-ylamino)propoxy]-benzoyl]piperidine S',S'-dioxide A stirred mixture of 0.15 g. of 4-(aminosulfonyl)-N-[3-[3-(1-piperidinylcarbonyl)phenoxy]propyl]-3-thiophenecarboxamide in 15 ml. of phosphorus oxychloride is heated under reflux for 30 minutes. The solution is evaporated in a rotary evaporator and the residue is triturated with 20 ml. of water. About 5 ml. of ethanol is added to the mixture to crystallize the oil which forms. The solid is collected and is air dried to give 65 mg. of product. The product is recrystallized twice from ethanol to give the analytical sample, m.p. 230°-232° C. The IR spectrum of this compound is identical with the IR spectrum of the product prepared by Method B, below. Also, no depression of the mixture melting point of the two products is observed.

Analysis for: $C_{20}H_{23}N_3O_4S_2$. Calculated: C, 55.40; H, 5.35; N, 9.69. Found: C, 55.18; H, 5.56; N, 9.30.

Method B

1-[3-[3-(thieno[3,4-d]isothiazol-3-ylamino)propoxy]benzoyl]piperidine S',S'-dioxide A mixture of 0.52 g. (0.002 mole) of 1-[[3-(3-aminopropoxy)phenyl]carbonyl]piperidine and 0.44 g. (0.002 mole) of 3-(methylthio)thieno[3,4-d]isothiazole 1,1-dioxide in 20 ml. of ethanol is heated under reflux for 1 hour. The mixture is filtered to give 0.5 g. of product. This material is recrystallized from ethanol to afford 0.2 g. of product, m.p. 232°-234° C.

Analysis for: $C_{20}H_{23}N_3O_4S_2$. Calculated: C, 55.40; H, 5.35; N, 9.69. Found: C, 55.00; H, 5.29; N, 9.46.

EXAMPLE 2

N-[3-[3-(1-piperidinylmethyl)phenoxy]propyl]-thieno[3,4-d]-isothiazole-3-amine 1,1-dioxide, hydrochloride A mixture of 0.2 g. (0.00046 mole) of 1-[3-[3-thieno[3,4-d]isothiazol-3-ylamino)propoxy]benzoyl]-piperidine S',S'-dioxide in 10 ml. of phosphorus oxychloride is warmed to give a solution. The heat is removed and the solution is stirred at room temperature for 15 minutes. The solution is evaporated at room temperature using a vacuum pump. To the residue is added 10 ml. of 1,2-dimethoxyethane. The solution is cooled in ice and 0.07 g. (0.0018 mole) of sodium borohydride is added. The ice is removed and the mixture is stirred at room temperature for 1 hour. The mixture is cooled in ice and 5 ml. of 10% aqueous hydrochloric acid solution is added dropwise. The mixture is evaporated using a vacuum pump and 20 ml. of water is added. The mixture is heated under reflux for 20 minutes, is cooled and is filtered. The filtrate is made basic with sodium carbonate and the resulting precipitate is collected. The filter cake is dissolved in ethanol and this solution is acidified with an etheral hydrochloric acid solution. The precipitate which forms is collected to give 60 mg. of product. The product is recrystallized from aqueous ethanol to afford the analytical sample, m.p. 256°-259° C. The IR spectrum of this material is identical to the IR spectrum of the compound which is prepared through an alternate route in U.S. Ser. No. 468,221. No depression of the mixture melting point of the two products is observed.

Analysis for: $C_{20}H_{25}N_3O_3S_2.HCl$. Calculated: C, 52.68; H, 5.75; N, 9.21. Found: C, 52.36; H, 5.71; N, 8.91.

EXAMPLE 3

The following compounds are prepared following the procedure of Example 1, using the appropriate starting intermediates:

(A)

N-[3-[3-(1-piperidinylmethyl)phenoxy]propyl]-thieno[2,3-d]isothiazol-3-amine 1,1-dioxide, m.p. 132°-5° C.

Analysis for: $C_{20}H_{25}N_3O_3S_2$. Calculated: C, 57.25; H, 6.01, 10.02. Found: C, 56.92; H, 6.37; N, 10.05.

(B)

N-[3-[3-[(dipropylamino)methyl]phenoxy]propyl]-thieno[3,4-d]isothiazol-3-amine 1,1-dioxide, m.p. 184°-7° C.

Analysis for: $C_{21}H_{29}N_3O_3S_2.HCl$. Calculated: C, 53.43; H, 6.41; N, 8.90; Cl, 7.51. Found: C, 53.61; H, 6.45; N, 9.16; Cl, 7.63.

(C)

N-[3-[4-(1-piperidinylmethyl)phenoxy]propyl]-thieno[3,4-d]isothiazol-3-amine 1,1-dioxide, m.p. 137°-9° C.

Analysis for: $C_{20}H_{25}N_3O_3S_2$. Calculated: C, 57.25; H, 6.01; N, 10.02. Found: C, 57.16; H, 5.89; N, 9.93.

What is claimed is:

1. A compound having the formula

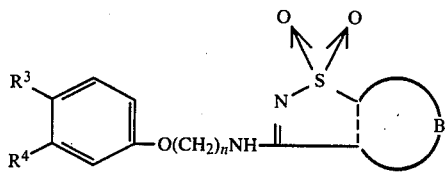

wherein

B is a moiety having the formula

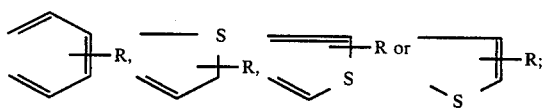

R is mono- or dihalo, nitro, cyano, trifluoromethyl, lower alkyl, lower alkoxy, lowercycloalkyl, mono- or di-lower alkyl substituted amino, lower alkyl thio, loweralkylsulfonyl, sulfamoyl, lower alkyl substituted sulfamoyl, phenyl or phenyl substituted with halo, lower alkyl, lower alkoxy, trifluoromethyl, cyano or nitro;

$R^3$ and $R^4$ are, independently, hydrogen or

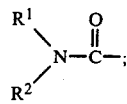

$R^1$ and $R^2$ are each independently hydrogen or lower alkyl; or $R^1$ and $R^2$ taken together form a heterocyclic moiety selected from the group 1-pyrrolidinyl, 1-piperidinyl, 1-hexahydroazepinyl, 1-octahydroazocinyl, 3-thiazolidinyl, 4-morpholinyl or 5-thiomorpholinyl, with the proviso that one of $R^3$ and $R^4$ is always hydrogen; and n is 1 to 4.

2. The compound of claim 1 having the name 1-[3-[3-(thieno[3,4-d]isothiazol-3-ylamino)propoxy]benzoyl]-piperidine S',S'-dioxide.

3. The compound of claim 1 having the name 1-[3-[3-(thieno[2,3-d]isothiazol-3-ylamino)propoxy]benzoyl]-piperidine S',S'-dioxide.

4. The compound of claim 1 having the name N-[3-[3-(thieno[3,4-d]isothiazol-3-ylamino)propoxy]benzoyl]dipropylamine S',S'-dioxide.

5. The compound of claim 1 having the name 1-[4-[3-(thieno[3,4-d]isothiazol-3-ylamino)propoxy]benzoyl]-piperidine S',S'-dioxide.

* * * * *